United States Patent [19]

Smith, Jr. et al.

[11] 4,148,896
[45] Apr. 10, 1979

[54] ANTIDEPRESSANT COMBINATION

[75] Inventors: Dewey H. Smith, Jr., Wilmington; Vernon G. Vernier, Newark, both of Del.

[73] Assignee: E. I. Du Pont de Nemours and Company, Wilmington, Del.

[21] Appl. No.: 880,067

[22] Filed: Feb. 22, 1978

[51] Int. Cl.$^2$ ...................... A61K 27/00; A61K 3/135
[52] U.S. Cl. ................................. 424/248.56; 424/330
[58] Field of Search ........................... 424/248.56, 330

[56] References Cited

U.S. PATENT DOCUMENTS 3,947,579  3/1976  Fuxe .................................... 424/267

OTHER PUBLICATIONS

Chem. Abst., vol. 85 –72339v (1976).

Primary Examiner—Stanley J. Friedman

[57] ABSTRACT

Amantadine and molindone or their pharmaceutically suitable salts, useful for treatment of depression.

10 Claims, 3 Drawing Figures

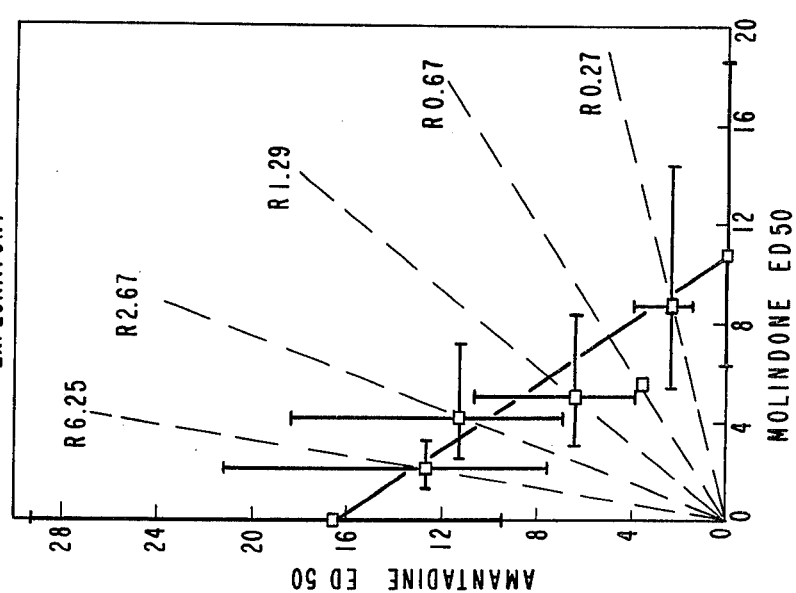
FIG. 1b BLOCKADE OF TETRABENAZINE-INDUCED SEDATION EXPLORATORY
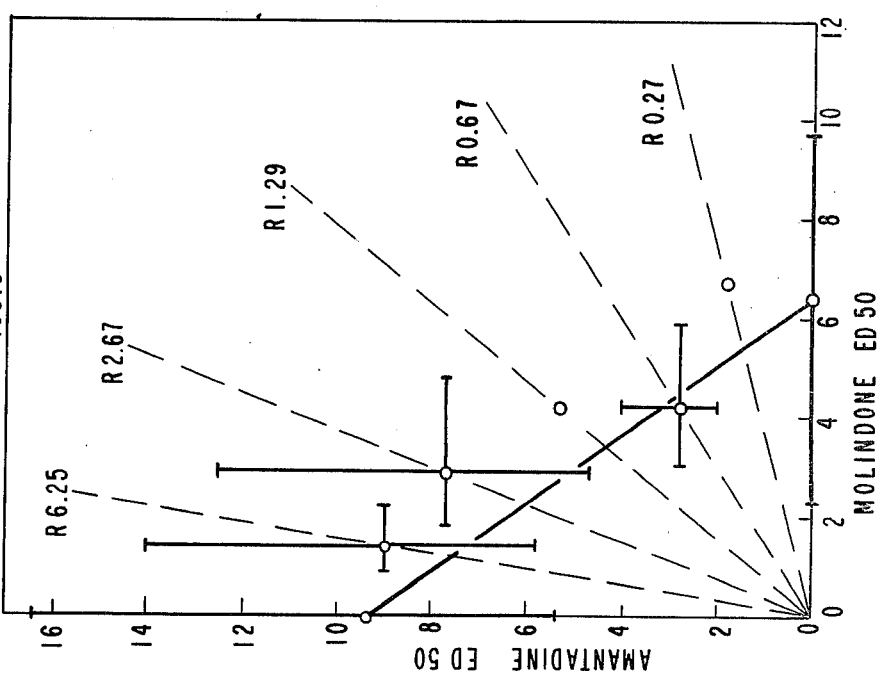
FIG. 1a BLOCKADE OF TETRABENAZINE-INDUCED SEDATION PTOSIS

ANTIDEPRESSANT COMBINATION

BACKGROUND OF THE DISCLOSURE

This invention relates to antidepressant combinations of amantadine and molindone, or their pharmaceutically suitable acid addition salts.

Amantadine (1-adamantanamine), particularly in its salt form as amantadine hydrochloride, is an anti-viral agent effective against $A_2$ (Asian) influenza in animals and man, and is effective for treatment of parkinsonism.

Molindone (3-ethyl-6,7-dihydro-2-methyl-5-(morpholinomethyl)indol-4(5H)-one), particularly in salt form as molindone hydrochloride, is known to have antipsychotic properties.

Mental illness encompasses both psychoses and neuroses. Symptoms requiring treatment include depression, anxiety, agitation, and hallucinations. Among the drugs used particularly for treatment of both reactive and endogenous depressions are monoamine oxidase (MAO) inhibitors, such as iproniazide, tranylcypromine, nialamide, phenelzine, and pargyline, and the non-MAO-inhibiting tricyclic aromatic dibenzazepines, such as imipramine, and dibenzocycloheptenes such as amitriptyline.

All of these drugs have adverse side effects that limit their usefulness. MAO inhibitors may benefit milder forms of depression, but the risk of serious toxic effects is a strong argument against their use. They can cause liver damage and acute hypertension, especially if given in conjunction with cheese, bananas, or other amine-containing foods. The MAO inhibitors can also cause tremors, insomnia, hyperhydrosis, agitation, hypermanic behavior, confusion, hallucinations, convulsions and orthostatic hypotension. They frequently cause dizziness, vertigo, headache, inhibition of ejaculation, difficulty in urination, weakness, fatigue, dry mouth, constipation and blurred vision.

Imipramine can cause blurred vision, dryness of mouth, constipation, urinary retention, orthostatic hypotension, respiration depression, myocardial infarction, and congestive heart failure. Similar difficulties are experienced with amitriptyline.

There is a continuing need for psychotherapeutic agents that have fewer side effects than the drugs in use today; also for psychotherapeutic agents that have different modes of action than presently used agents, since none of these is completely effective.

The present invention results from efforts to develop new, safe, and effective psychotherapeutic compositions with minimal side effects.

SUMMARY OF THE INVENTION

According to this invention there is provided novel compositions of amantadine and molindone and their pharmaceutically suitable acid addition salts and methods of using such compositions to alleviate depression in mammals.

Pharmaceutical Salts

Pharmaceutically suitable acid addition salts of amantadine and molindone include those made with physiologically acceptable acids that are known in the art; such salts include hydrochloride, sulfate, phosphate, nitrate, citrate, maleate, and the like. A preferred salt for both amantadine and molindone is the hydrochloride.

Figures

FIGS. 1a and 1b are graphs showing the interaction of amantadine and molindone on Tetrabenazine-induced sedation in mice.

Detailed Discussion of the Invention

Figure 2:
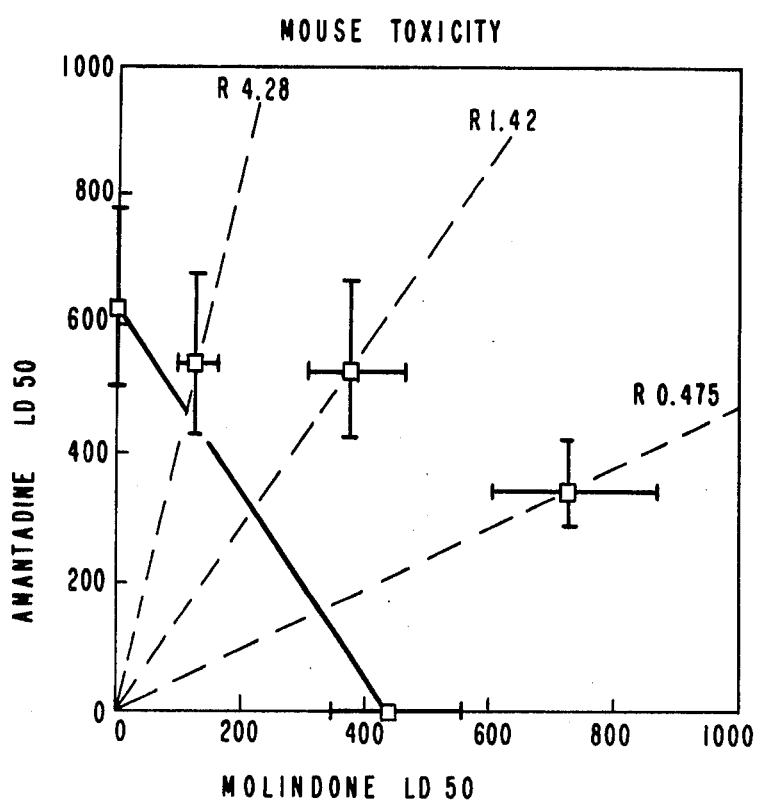
FIG. 2 is a graph showing toxicity of amantadine and molindone in mice.

As employed herein, amantadine is employed in its normal definition, namely, 1-adamantanamine which has the structure:

Molindone refers to 3-ethyl-6,7-dihydro-2-methyl-5-(morpholinomethyl)indol-4-(5H)-one which has the structure:

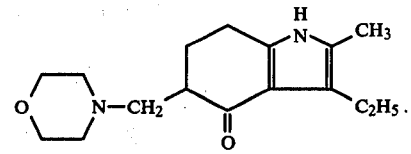

Both amantadine and molindone and their pharmaceutically suitable acid addition salts, particularly the hydrochloride, have antidepressant activity. These two drugs in combination have been shown to result in a decrease of toxicity since it has been demonstrated in mice that amantadine hydrochloride reduces molindone hydrochloride lethal toxicity (mortality).

Since both amantadine and molindone and their pharmaceutically suitable salts have antidepressant properties, the ratios of these components to one another can vary greatly for alleviating depression in mammals. A suitable ratio (by weight) of amantadine or its pharmaceutically suitable salt to molindone or its pharmaceutically salt is in a range from 20:1 to 0.01:1. A more preferred range for reducing toxicity ranges from 5:1 to 0.05:1 and more preferable 3:1 to 0.2:1.

Dosage Forms and Use

The combination of amantadine or molindone or its salt can be administered as treatment for psychiatric depressions of the reactive and endogenous types by any means that produces contact of the active agent with the agent's site of action in the body of a mammal. In addition to antidepressant activity, the combination also has a beneficial sedative action. The amantadine and molindone can be administered by any conventional means available fo use in conjunction with pharmaceuticals; either in combination with one another or in combination with other therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of total active ingredient can be about 0.1 to 5 milligrams per kilogram of body weight. Ordinarily 0.2 to 2 and preferably 0.4 to 1 milligrams per kilogram per day given in divided doses 3 to 4 times a day or in sustained release form is effective to obtain desired results.

The active ingredient can be administered orally in solid dosage forms, such as capsules, tablets, and powders, or in liquid dosage forms, such as elixirs, syrups, and suspensions; it can also be administered parenterally, in sterile liquid dosage forms; or rectally in the form of suppositories.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and protect the tablet from the atmosphere, or enteric-coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA (ethylenediaminetetraacetic acid). In addition, parenteral solutions can contain preservatives, such as benzalkonium chloride, methyl- or propyl-paraben, and chlorobutanol.

Suppositories contain the active ingredient in a suitable oleaginous or water-soluble base. The oleaginous class includes cocoa butter and fats with similar properties: the water-soluble class includes polyethylene glycols.

Suitable pharmaceutical carriers are described in *Remington's Pharmaceutical Sciences*, E. W. Martin, a standard reference text in this field.

Useful pharmaceutical dosage-forms for administration of the compounds of this invention can be illustrated as follows:

Capsules

Capsules can be prepared by filling standard two-piece hard gelatin capsules with the following mixture using conventional encapsulating equipment:

| Active ingredients | 10 or 25 mg. |
|---|---|
| Lactose | 225 mg. |
| Talc | 25 mg. |
| Magnesium stearate | 8 mg. |

Capsules

A mixture of active drugs in soybean oil is prepared and injected by means of a positive displacement pump in gelatin to form soft gelatin capsules containing 25 mg. total of the active ingredients. The capsules are washed in petroleum ether and dried.

Tablets

Tablets can be prepared by conventional procedures so that each unit will contain:

| Active ingredients | 10 or 25 mg. |
|---|---|
| Spray dried lactose | 100 mg. |
| Microcrystalline cellulose | 50 mg. |
| Magnesium stearate | 3 mg. |

Parenteral

Parenteral composition suitable for intramuscular administration is prepared so that each ml. contains:

| Active ingredients | 10 mg. |
|---|---|
| Sodium carboxy methyl cellulose | 0.75% |
| Polysorbate 80 | 0.04% |
| Benzyl alcohol | 0.9% |
| Sodium chloride | 0.9% |
| Water for injection Q.S. | 1 ml. |

Suspension

An aqueous suspension is prepared for oral administration so that each 5 mls. contain:

| Active ingredients | 10 mg. |
|---|---|
| Methylcellulose | 5% |
| Carboxy methyl cellulose | 5% |
| Syrup | 30% |
| Polysorbate 80 | 0.2% |
| Sodium saccharin | 2 mg. |
| Cherry flavor | 0.1% |
| Sodium benzoate | 5 mg. |
| Water Q.S. | 5 ml. |

Test Methods

Carworth Farms $CF_1S$ female white mice were used throughout. Animals weighing 18–22 g each and fasted one hour were used in the antidepressant test, while mice weighing 17.5–18.5 g each and fasted 17–18 hours were used in the toxicity study. All mice were dosed orally with coded doses (calculated as free base) of amantadine hydrochloride and molindone hydrochloride. The drugs were dissolved in water as vehicle. The dosing volume was always 10 ml/kg.

A. MOUSE ANTIDEPRESSANT TEST

A standard procedure for detecting and comparing the antidepressant activity of compounds in this series for which there is good correlation with human efficacy is the prevention of tetrabenazine-induced sedation and depression in mice. (Everett, "The Dopa Response Potentiation Test and Its Use in Screening for Antidepressant Drugs," pp. 164–167 in "Antidepressant Drugs" [Proceedings of the First International Symposium], S. Garattini and M. N. G. Dukes, eds., 1967.).

Mice, intubated with amantadine hydrochloride or vehicle, and molindone hydrochloride or vehicle, were injected intraperitoneally with 32 mg/kg tetrabenazine (as the methanesulfonate, dissolved in 0.20 ml 0.05 M. KCl at pH 2.0). 30 Minutes after administration of tetrabenazine, the mice were examined for signs of blepharoptosis (eyelid closure) and exploratory activity. Normal exploratory activity (relief from sedation) was recorded when a mouse lifted by the tail from a group of 10 in a testing box and placed on a stainless steel testing box lid (12.5"×5" with 0.33" mesh) either turned its head horizontally 30° in both directions or moved to the edge of the screen within 10 seconds after being placed on the screen. Relief from ptosis was recorded when exactly two seconds after placing the mouse facing the observer, lid closure was less than 50% in both eyes.

Initially the time of peak activity was determined separately for each drug in the antidepressant test. Then several doses of each drug alone and in precise amantadine hydrochloride/molindone hydrochloride ratios were given orally. Each mouse received two intubations, one of amantadine hydrochloride or vehicle and one of molindone hydrochloride or vehicle, at times such that observations were started at or near the times of peak antidepressant effect.

The oral dose and time response data for mice given amantadine hydrochloride or molindone hydrochloride are in Table 1. Peak time for amantadine was at one hour, Ptosis ED50=9.4 mg/kg. Peak time for molindone hydrochloride was ca. 4-6 hours, Ptosis ED50=7.2 mg/kg. For the purpose of studying the effects of both amantadine hydrochloride and molindone hydrochloride in the same tetrabenazine-sedated mice, 4 hours after molindone hydrochloride was taken represented peak time for antitetrabenazine activity.

The interaction of amantadine hydrochloride and molindone hydrochloride on tetrabenazine-induced sedation in mice is demonstrated by the data in Table 2 and Loewe isobolograms (S. Loewe: Pharm. Rev., 9, 237-242, 1957) in FIGS. 1a and 1b. In these figures the diagonal lines joining the ED50 values of the 2 drugs given separately represents additivity of drug effects. ED50's falling under the curve (between the line and the origin) indicate potentiation while those outside the curve suggest antagonism between the two drugs. The five diagonal lines radiating from the origin represent the dose ratios of amantadine to molindone used in mice which received both drugs. The horizontal and vertical bars through each ED50 point are the 95% confidence limits. FIGS. 1a and 1b show that the antitetrabenazine activity of the two drugs is additive for all ratios of amantadine to molindone, since all the confidence limits overlap the line of additivity.

B. MOUSE TOXICITY TEST

In the toxicity study, the amantadine hydrochloride doses (or vehicle) were followed 2.5 minutes later by the molindone hydrochloride doses (or vehicle). The mice were kept in Lucite ® acrylic observation chambers (4½"×5"×5" with ¼" Hardware Screen floor) without handling for 4 hours after dosing, then they were placed in holding boxes with AB-SORB-DRI ® litter for the remainder of the 336 hours observation period. The numbers of dead mice were recorded at 0.5, 1, 2, 4, 6 and 24 hours and each 24 hours thereafter until the end of test.

The toxicity data are in Table 3 and the ED50's also are plotted in FIG. 2. At the high amantadine/-molindone ratio the drug effects were additive, but there was significant antagonism at the other 2 ratios. FIG. 2 is considered to demonstrate that amantadine decreases the toxicity of molindone.

C. TRYPTAMINE POTENTIATION TEST

In this test for detection of MAO inhibitors and also serotonergic agents as well, 60 mg/kg tryptamine HCl was given intravenously 55 minutes after oral test drug. At 5 minutes after tryptamine injection the mice were observed for 30 seconds for stereotyped head turning, twitching and convulsing with "piano player" type movements of the front feet and for flaccid paralysis of the hind limbs. (60 Mg/kg of tryptamine alone causes this syndrome but it lasts for less than a minute, usually only a few seconds.) The data were analyzed quantally and ED50's calculated.

The data are in Table 4. Molindone potentiates the action of tryptamine in a dose-related manner giving ED50's=15 for head twitch (peak time=6 hours) and 8.6 for hind limb paralysis (peak time=4 hours). These peak times correspond to those for peak activity in the antitetrabenazine test. At higher doses the potentiation of tryptamine disappears, also in a dose-related fashion. This type of dose-response is not ordinarily given by standard MAO inhibitor drugs.

D. MAO INHIBITION TEST, IN VITRO

For brain MAO studies, 10-20 g mice were killed, their brains were excised quickly, were dropped into ice cold 0.1 M phosphate pH 7.4 (10 ml/gram wet tissue), and were homogenized for 5 minutes with ice chilling. The homogenate was stored at ice temperature until used. 20-Ml test beakers were prepared with 1 ml homogenate and 0.5 ml test drug or water and were preincubated 10 minutes at 37° C. with shaking in air using a Dubnoff metabolic incubator. 0.5 Ml of the substrate (5-hydroxytryptamine, or 5 HT) at $2\times10^{-4}$ M was added and the samples, 3 per dose and 3 with substrate but not enzyme, were incubated for 60 minutes. The reaction was stopped by addition of 2 ml 0.5 M borate, pH 10.5. Two grams NaCl was added and the samples were extracted with 7 ml borate-washed n-butanol and centrifuged. Three ml of each n-butanol extract plus 5 ml of HCl-washed n-heptane were back-extracted with 1.5 ml 0.1 N HCl and were centrifuged. The organic layer was aspirated off and 1 ml of each 0.1 N HCl extract was mixed with 1 ml 6 N HCl. Fluorescence was measured at 540 nm with excitation at 290 nm and mean values were determined. Percent inhibition $P_I$ was calculated by $$P_I = \frac{F_I - F_O}{F_S} \cdot 100$$

$F_I$=fluorescence of test drug sample, $F_O$=fluorescence of uninhibited sample and $F_S$=fluorescence of the substrate-only sample. Percent inhibition versus inhibitor concentration was plotted and the KI50% (concentration for 50% inhibition) was estimated either graphically or by linear regression analysis.

All ED50 and LD50 values were determined numerically by the moving average method of Thompson (W. F. Thompson: *Bacteriological Reviews*, 11, 115-145, 1947) and 95% confidence limits were calculated according to Litchfield (J. T. Litchfield, Jr. and F. Wilcoxon: *J. Pharm. Exptl. Therap.*, 96, 99, 1949).

Table 5 contains the simultaneously obtained data for molindone hydrochloride and for the inhibitor standard, phenelzine. Molindone hydrochloride was virtually inactive at the high concentration of $1\times10^{-3}$ M while the KI50 for phenelzine was $4\times10^{-6}$ M. From these data molindone clearly cannot act as an antidepressant by means of a MAO inhibitor mechanism.

"Consisting essentially of" in the present disclosure is intended to have its customary meaning: namely, that all specified materials and conditions are very important in practicing the invention but that unspecified materials and conditions are not excluded so long as they do not prevent the benefits of the invention from being realized.

TABLE 1

TIME AND DOSE RESPONSES OF AMANTADINE AND MOLINDONE ORALLY IN THE MOUSE ANTITETRABENAZINE TEST
(N = 10)

| | | NUMBER OF MICE BLOCKED | | | | | | | | | | | | |
|---|---|---|---|---|---|---|---|---|---|---|---|---|---|---|
| | | PTOSIS HOURS | | | | | | | EXPLORATORY ACTIVITY HOURS | | | | | |
| DRUG | DOSE[a] mg/kg | 0.5 | 1 | 2 | 3 | 4 | 6 | 24 | 0.5 | 1 | 2 | 3 | 4 | 6 | 24 |
| | 1 | — | 1 | — | — | — | — | — | | 0 | — | — | — | — | — |
| | 3 | — | 1 | — | — | — | — | — | | 0 | — | — | — | — | — |
| Amantadine | 9 | — | 5 | — | — | — | — | — | | 4 | — | — | — | — | — |
| | 20[b] | 4 | 13 | 11 | — | 2 | — | — | 1 | 8 | 6 | — | 0 | — | — |
| | 27 | — | 7 | — | — | — | — | — | | 4 | — | — | — | — | — |
| | 81 | — | 10 | — | — | — | — | — | | 8 | — | — | — | — | — |
| | ED50[a] mg/kg | | 9.6 | | | | | | | 24 | | | | | |
| | 0 | — | 0 | 0[c] | — | 0 | — | — | — | 0 | 0 | — | 0 | — | — |
| | 1 | — | 0 | 0 | — | 0 | — | — | — | 0 | 0 | — | 0 | — | — |
| | 3 | — | 0 | 1 | — | 0 | — | — | — | 0 | 0 | — | 0 | — | — |
| Molindone | 9 | — | 0 | 5 | — | 7 | — | — | — | 0 | 3 | — | 5 | — | — |
| | 13[b] | — | 0 | 8 | 19 | 20 | 20 | 10 | — | 0 | 6 | 16 | 19 | 20 | 6 |
| | 27 | — | 0 | 10 | — | 10 | — | — | — | 0 | 10 | — | 10 | — | — |
| | 81 | — | 0 | 10 | — | 10 | — | — | — | 0 | 10 | — | 10 | — | — |
| | ED50[a] mg/kg | | >81 | 8.5 | | 7.2 | | | | >81 | 11.2 | | 9 | | |

[a]Free base basis.
[b]N = 20
[c]N = 30

TABLE 2

ANTIDEPRESSANT ACTIVITY OF AMANTADINE + MOLINDONE IN THE MOUSE ANTITETRABENAZINE TEST
The test was performed 1 hour after oral amaniadine and 4 hours after oral molindone; N = 20.

| | | | ANTAGONISM OF TETRABENAZINE-INDUCED SEDATION | | | | | |
|---|---|---|---|---|---|---|---|---|
| | | | PTOSIS | | | EXPLORATORY ACTIVITY | | |
| Ratio = (Amantadine/ Molindone) | DRUG DOSE - mg/kg[a] | | No. of Mice Blocked | ED50/95% Confidence Limits | | No. of Mice Blocked | ED50/(95% Confidence Limits | |
| | Amantadine | Molindone | | Amantadine | Molindone | | Amantadine | Molindone |
| — | 0 | 0 | 0 | 9.4 | — | 0 | 16.6 | — |
| | 2 | 0 | 2 | (5.4,16.4) | | 0 | (9.4,29.2) | |
| | 6 | 0 | 4 | | | 2 | | |
| | 18 | 0 | 17 | | | 12 | | |
| | 54 | 0 | 19 | | | 16 | | |
| 6.25 | 1.67 | 0.27 | 3 | 0.0 | 1.4 | 0 | 12.7 | 2.1 |
| | 5 | 0.8 | 2 | (5.8,14.0) | (0.89, 2.2) | 0 | (7.6,21.2) | (1.3, 3.3) |
| | 15 | 2.4 | 16 | | | 13 | | |
| | 45 | 7.2 | 20 | | | 20 | | |
| 2.67 | 1.33 | 0.5 | 0 | 7.7 | 2.9 | 0 | 11.3 | 4.2 |
| | 4 | 1.5 | 1 | (4.7,12.5) | (1.8, 4.8) | 1 | (6.9,18.4) | (2.5, 7.1) |
| | 12 | 4.5 | 17 | | | 12 | | |
| | 36 | 13.5 | 20 | | | 18 | | |
| 1.29 | 1 | 0.78 | 0 | 5.3[b] | 4.2[b] | 0 | 6.4 | 5.0 |
| | 3 | 2.33 | 1 | | | 0 | (3.9,10.6) | (3.0,8.4) |
| | 9 | 7. | 19 | | | 17 | | |
| | 27 | 21. | 19 | | | 19 | | |
| 0.67 | 0.67 | 1 | 0 | 2.8 | 4.2 | 0 | 3.7[b] | 5.5[b] |
| | 2 | 3 | 4 | (2.0,4.0) | (3.0,5.9) | 1 | | |
| | 6 | 9 | 20 | | | 18 | | |
| | 18 | 27 | 20 | | | 20 | | |
| 0.27 | 0.33 | 1.22 | 0 | 1.8[b] | 6.7[b] | 0 | 2.4 | 8.8 |
| | 1 | 3.67 | 1 | | | 0 | (1.5,3.9) | (5.4,14.5) |
| | 3 | 11 | 18 | | | 14 | | |
| | 9 | 33 | 20 | | | 20 | | |
| 0 | 0 | 1.5 | 1 | — | 6.4 | 0 | — | 10.8 |
| | 0 | 4.5 | 5 | | (3.7,11.1) | 2 | | (6.3,18.8) |
| | 0 | 13.5 | 18 | | | 12 | | |
| | 0 | 40.5 | 20 | | | 20 | | |

[a]Free base basis.
[b]95% Confidence limits not calculatable by Litchfield-Wilcoxon method.

TABLE 3

TOXICITY OF AMANTADINE + MOLINDONE ORALLY IN MICE N=10

| RATIO = (Amantadine/ Molindone) | DRUG DOSE - mg/kg[a] | | NUMBER OF MICE DEAD HOURS | | | | | | 24 HR. LD50 (95% Confidence Limits) | |
|---|---|---|---|---|---|---|---|---|---|---|
| | Amantadine | Molindone | 0.5 | 1 | 2 | 4 | 24 | 336 | Amantadine | Molindone |
| 0 | 0 | 0 | 0 | 0 | 0 | 0 | 0 | 0 | — | 440 (347,558) |
| | 0 | 212 | 0 | 0 | 0 | 0 | 0 | 0 | | |
| | 0 | 318 | 2 | 2 | 2 | 2 | 2 | 2 | | |
| | 0 | 477 | 3 | 5 | 5 | 5 | 5 | 5 | | |
| | 0 | 716 | 7 | 7 | 7 | 9 | 10 | 10 | | |
| | 0 | 1073 | 9 | 9 | 9 | 10 | 10 | 10 | | |
| 0.475 | 0 | 0 | 0 | 0 | 0 | 0 | 0 | 0 | 344 (286,414) | 725 (605,868) |
| | 72 | 151 | 0 | 0 | 0 | 0 | 0 | 0 | | |
| | 107 | 226 | 0 | 0 | 0 | 0 | 0 | 0 | | |
| | 161 | 339 | 0 | 1 | 1 | 1 | 2 | 2 | | |
| | 263 | 509 | 1 | 1 | 1 | 3 | 3 | 3 | | |
| | 343 | 763 | 0 | 0 | 0 | 0 | 3 | 3 | | |
| | 544 | 1145 | 6 | 6 | 9 | 10 | 10 | 10 | | |
| 1.42 | 0 | 0 | 0 | 0 | 0 | 0 | 0 | 0 | 532 (425,666) | 374 (303,462) |
| | 140 | 98 | 0 | 0 | 0 | 0 | 0 | 0 | | |
| | 210 | 147 | 0 | 0 | 0 | 0 | 0 | 0 | | |
| | 314 | 221 | 0 | 0 | 0 | 0 | 0 | 0 | | |
| | 471 | 331 | 2 | 3 | 3 | 3 | 5 | 5 | | |
| | 707 | 497 | 3 | 3 | 3 | 4 | 7 | 7 | | |
| | 1001 | 745 | 8 | 8 | 9 | 9 | 10 | 10 | | |
| 4.28 | 0 | 0 | 0 | 0 | 0 | 0 | 0 | 0 | 541 (430,681) | 126 (98,163) |
| | 215 | 50 | 0 | 0 | 0 | 0 | 0 | 0 | | |
| | 322 | 75 | 0 | 0 | 0 | 0 | 1 | 1 | | |
| | 483 | 113 | 0 | 0 | 0 | 1 | 2 | 2 | | |
| | 725 | 170 | 9 | 9 | 9 | 9 | 10 | 10 | | |
| | 1088 | 254 | 10 | 10 | 10 | 10 | 10 | 10 | | |
| — | 0 | 0 | 0 | 0 | 0 | 0 | 0 | 0 | 626 (504,777) | — |
| | 267 | 0 | 0 | 0 | 0 | 0 | 0 | 0 | | |
| | 400 | 0 | 1 | 1 | 1 | 1 | 1 | 1 | | |
| | 600 | 0 | 4 | 4 | 4 | 4 | 5 | 5 | | |
| | 900 | 0 | 8 | 8 | 8 | 8 | 8 | 8 | | |
| | 1350 | 0 | 10 | 10 | 10 | 10 | 10 | 10 | | |

[a]Free base basis.

TABLE 4

MOLINDONE POTENTIATES TRYPTAMINE-INDUCED STEREOTYPIES AND HIND LIMB PARALYSIS IN MICE
N = 10

| DOSE mg/kg p.o. | HEAD TWITCH | | | | | HIND LIMB PARALYSIS | | | | |
|---|---|---|---|---|---|---|---|---|---|---|
| | 1 Hr. | 2 Hrs. | 4 Hrs. | 6 Hrs. | 24 Hrs. | 1 Hr. | 2 Hrs. | 4 Hrs. | 6 Hrs. | 24 Hrs. |
| 0 | 0 | 0 | 0[a] | 0 | 0 | 0 | 0 | 0[a] | 0 | 0 |
| 2.5 | — | — | 0 | — | — | — | — | 0 | — | — |
| 5. | — | — | 0 | — | — | — | — | 1 | — | — |
| 10. | 1 | 2 | 1[a] | 0 | 0 | 3 | 8 | 13[a] | 7 | 0 |
| 20. | 3 | 3 | 17[a] | 9 | 0 | 9 | 10 | 20[a] | 10 | 0 |
| 40. | 5 | 5 | 19[a] | 9 | 0 | 10 | 10 | 20[a] | 10 | 0 |
| 80. | 0 | 1 | 3 | 6 | 0 | 4 | 4 | 6 | 10 | 0 |
| 160. | 0 | 0 | 0 | 0 | 2 | 1 | 4 | 2 | 4 | 2 |
| ED50 mg/kg p.o. | 40 | 40 | 16.7 | 15 | >160 | 13 | <10-8.6 | <10 | >160 | |

[a]N = 20 at this dose

TABLE 5

EFFECTS OF MOLINDONE AND PHENELZINE ON MOUSE BRAIN MAO, IN VITRO

| | FINAL CONC. m/l | % INHIBITION | KI50 m/l |
|---|---|---|---|
| MOLINDONE . HCl | $10^{-3}$ | 14 | $>1 \times 10^{-3}$ |
| | $10^{-4}$ | 1 | |
| | $10^{-5}$ | 1 | |
| | $10^{-6}$ | 0 | |
| PHENELZINE . SO$_4$ | $10^{-4}$ | 88 | $4 \times 10^{-6}$ |
| | $10^{-5}$ | 81 | |
| | $10^{-6}$ | 3 | |

What is claimed is:

1. A pharmaceutical composition consisting essentially of (a) amantadine or a pharmaceutically suitable acid addition salt thereof, and (b) molindone or a pharmaceutically suitable acid addition salt thereof, with a ratio of (a) to (b) in a range by weight from 20:1 to 0.01:1.

2. The composition of claim 1 which contains amantadine hydrochloride and molindone hydrochloride.

3. The composition of claim 1 which contains a pharmaceutically suitable carrier.

4. The composition of claim 1 wherein the ratio is in a range from 5:1 to 0.05:1.

5. The composition of claim 4 wherein the ratio is in a range from 3:1 to 0.2:1.

6. A method of alleviating depression in a mammal which comprises administering to the mammal an effective antidepressant amount of the composition of claim 1.

7. A method of alleviating depression in a mammal which comprises administering to the mammal an effective antidepressant amount of the composition of claim 2.

8. A method of alleviating depression in a mammal which comprises administering to the mammal an effective antidepressant amount of the composition of claim 3.

9. A method of alleviating depression in a mammal which comprises administering to the mammal an effective antidepressant amount of the composition of claim 4.

10. A method of alleviating depression in a mammal which comprises administering to the mammal an effective antidepressant amount of the composition of claim 5.

* * * * *